United States Patent [19]

Bauer

[11] Patent Number: 5,282,477
[45] Date of Patent: Feb. 1, 1994

[54] DEVICE FOR RELIABLY PERFORMING A BIOPSY, IN PARTICULAR A BONE-MARROW BIOPSY

[76] Inventor: Alberto Bauer, 44042 Cento (Ferrara), Corso Guercino, 56, Italy

[21] Appl. No.: 985,885

[22] Filed: Dec. 4, 1992

[30] Foreign Application Priority Data

Dec. 18, 1991 [IT] Italy .................. MI91 A 003394

[51] Int. Cl.⁵ .......................................... A61B 10/00
[52] U.S. Cl. ................................................ 128/754
[58] Field of Search ............... 128/749, 751, 753, 754; 606/167, 170

[56] References Cited

U.S. PATENT DOCUMENTS

| | | | |
|---|---|---|---|
| 2,623,521 | 12/1952 | Shaw | 128/754 |
| 4,010,737 | 3/1977 | Vilaghy et al. | 128/754 |
| 4,266,555 | 5/1981 | Jamshidi | 128/754 |
| 5,040,542 | 8/1991 | Gray | 128/754 |

*Primary Examiner*—Max Hindenburg
*Attorney, Agent, or Firm*—Ladas & Parry

[57] ABSTRACT

A device for performing a biopsy, in particular a bone-marrow biopsy, comprises a needle (1) provided with a handgrip (2) and a cannula (3) housing a mandrel (5) movable within the cannula bore (4). The handgrip (2) comprises a chamber (26) arranged coaxially with the cannula (3) and having two opposing ends, one (28) hermetically sealed and located in an edge (27) of the handgrip (2) and the other communicating with the bore (4) of the cannula (3), in correspondence with this latter there being provided interception means (11) operable from the outside of the handgrip (2) to lock the mandrel (5) within the cannula (3) during the insertion of the needle (1) into the patient but to enable the mandrel to move during the performing of the biopsy, the tissue which penetrates into the cannula (3) acting on the mandrel (5) to move the free end (8) of this latter into the chamber in the handgrip (2), said movement being measurable and providing confirmation that the biopsy has taken place and of the quantity of tissue which has penetrated into the cannula.

12 Claims, 1 Drawing Sheet

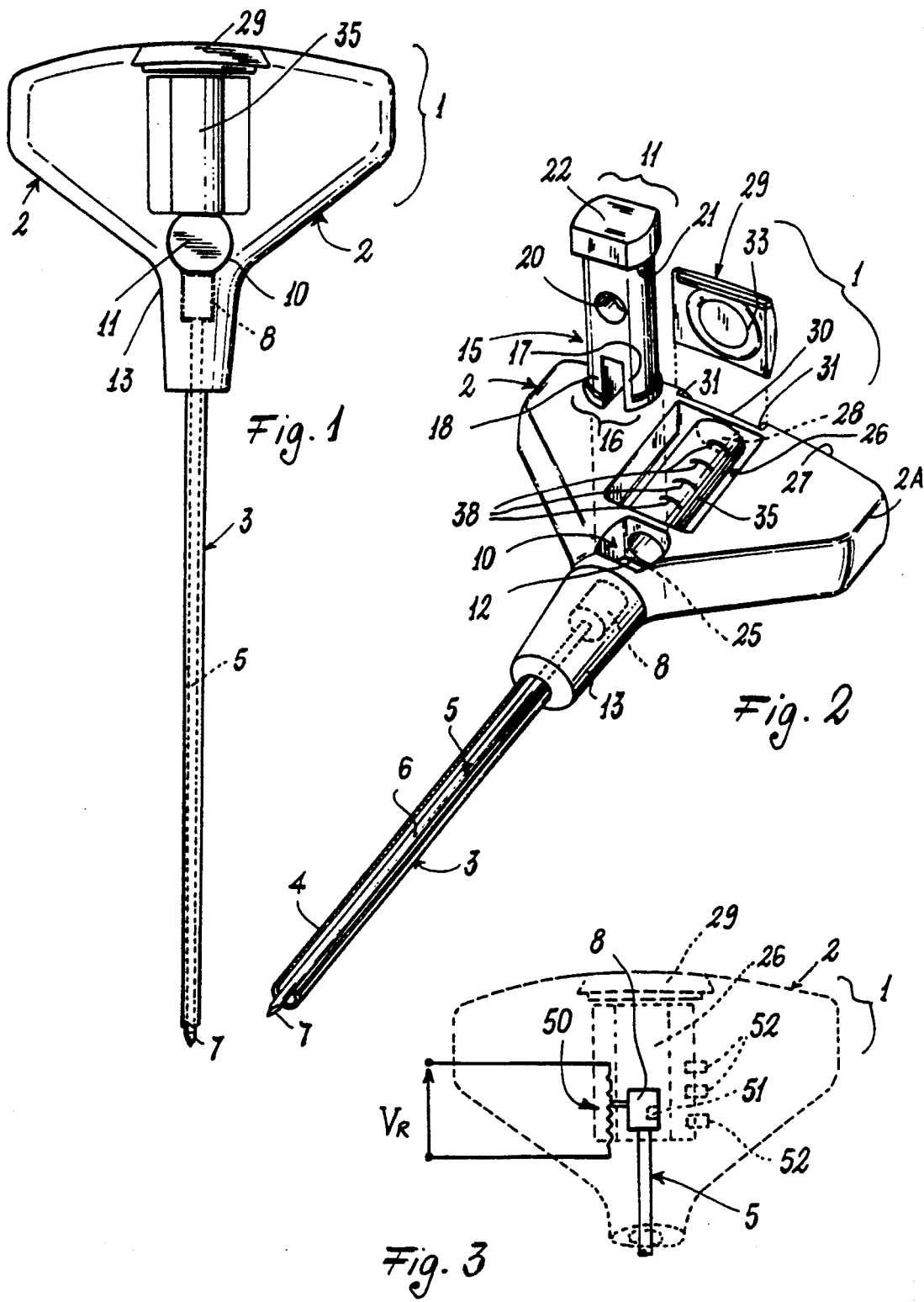

5,282,477

DEVICE FOR RELIABLY PERFORMING A BIOPSY, IN PARTICULAR A BONE-MARROW BIOPSY

FIELD AND BACKGROUND OF THE INVENTION

This invention relates to a device for performing a biopsy, in particular a bone-marrow biopsy, comprising a needle provided with a handgrip and a cannula housing a mandrel movable within the cannula bore.

With particular reference to a histological examination effected on a bone, the biopsy performed on the patient for this purpose can involve various problems relating to the quantity of bone tissue withdrawn and its retention during the extraction of the needle from the patient, if the needle is of known type.

In this respect, with known needles it can happen that during their extraction, the tissue is lost within the patient without the person performing the biopsy being aware of this. This means that the examination has to be performed a second time, with obvious inconvenience.

In addition the impossibility of knowing whether tissue has actually been withdrawn from the patient and how much tissue has been removed can create obvious problems both during the performing of the biopsy and during the histological examination.

SUMMARY OF THE INVENTION

An object of the invention is to provide a device of the stated type with which during the biopsy it is possible to know whether tissue has actually been removed from the patient.

A further object is to provide a device of the stated type which enables the quantity of tissue removed during the biopsy to be known.

A further object is to provide a device of the stated type with which it is possible to know whether the removed tissue has been lost from the cannula during the extraction of the needle from the patient.

A further object is to provide a device which is reliable in use, is of low cost and is simple to use.

These and further objects which will be apparent to the expert of the art are attained by a device of the stated type, characterised in that the handgrip comprises a chamber arranged coaxially with the cannula and having two opposing ends, one hermetically sealed and located in an edge of the handgrip and the other communicating with the bore of the cannula, in correspondence with this latter there being provided interception means operable from the outside of the handgrip to lock the mandrel within the cannula during the insertion of the needle into the patient but to enable the mandrel to move during the performing of the biopsy, the tissue which penetrates into the cannula acting on the mandrel to move the free end of this latter into the chamber in the handgrip, said movement being measurable and providing confirmation that the biopsy has taken place and of the quantity of tissue which has penetrated into the cannula.

BRIEF DESCRIPTION OF THE DRAWINGS

The present invention will be more apparent from the accompanying drawing, which is provided by way of non-limiting example and in which:

FIG. 1 is a front view of the device of the invention;

FIG. 2 is an exploded view of the device of FIG. 1 with some parts shown in section; and FIG. 3 is a schematic representation of a different embodiment of the device of FIG. 1.

DETAILED DESCRIPTION OF PREFERRED EMBODIMENTS

With reference to said figures, a biopsy needle is indicated overall by 1 and comprises a handgrip 2 to which a cannula 3 with a bore 4 is connected. The cannula is fixed in any known manner to the handgrip 2 such that it is unable to rotate relative to this latter. Inside the cannula there is a mandrel 5 comprising a shaft 6 terminating at one end 7 with a point and comprising a cap 8 at its other end.

The bore 4 of the cannula 3 communicates with a seat 10 for a cylindrical member 11 for locking the mandrel 5 in the cannula. The seat 10 is in the form of a through hole 11 with its axis perpendicular to the axis of the cannula 3, and provided in a tapered part 13 of the handgrip 2.

The member 11 comprises a stem 15 terminating at one end 16 with two opposing spaced arms 17 and 18 which are able to elastically approach each other. In the stem 15 there is provided a through hole 20 which when the member 11 is in its working position in the seat 10 is coaxial with the bore 4 of the cannula 3. At its other end 21 the stem 15 comprises an enlarged head 22 acting as a travel stop for the movement of the member 11 in the seat 10.

This latter is connected, via a channel 25 with its axis perpendicular to the axis of said seat, to a chamber 26 coaxial with the bore 4 of the cannula 3. This chamber communicates with the end edge 27 of the handgrip via an aperture 28 closable by a closure element 29. This latter is removable fixed to said edge 27 by being removably inserted into a seat 30 provided in said edge and comprising lateral guides 31 for the insertion of said element 29 and its retention by the handgrip 2.

The element 29 also supports a seal member 33 which cooperates with the aperture 28 in the chamber 26.

Finally, this latter comprises at least one transparent wall 35 (in a face 2A of the handgrip 2) to enable the interior of the chamber to be viewed. Advantageously, the wall 35 comprises markings 38 defining a scale for determining the position of the cap 8 of the mandrel 5 within the chamber 26.

The procedure for performing a bone-marrow biopsy is as follows. The needle 1 is inserted into the patient with the mandrel 5 locked inside the cannula 3. To achieve this, the locking member 11 is partly extracted from the seat 10 so that its through hole 20 is offset from the bore 4 of the cannula 3.

On reaching the region in which the biopsy is to be performed, the member 11 is completely inserted into its seat 10 (for example by pressing on the head 22 projecting from the hole 12) so as to bring the hole 20 coaxial with the bore 4 of the cannula 3.

The biopsy is then performed. In this manner the tissue which penetrates into the cannula 3 moves the mandrel 5 towards the handgrip 2. The cap 8 carried by said mandrel consequently passes into the channel 25 and reaches the chamber 26. As the biopsy proceeds, this cap increasingly penetrates into said chamber and reaches various positions therein. These positions, corresponding to different quantities of tissue removed from the bone subjected to biopsy, can be observed on the scale defined by the markings 38 present on the face 2A of the handgrip 2 at the transparent wall 35 of the chamber 26.

Likewise, on removing the needle 1 from the patient after performing the biopsy, if it is found that the cap 8 rigid with the mandrel 5 has remained in the position which it had reached in the chamber 26, this is proof that the tissue present in the cannula bore 4 has not been lost.

Consequently the invention makes it possible to confirm by the movement of the mandrel 5 within the chamber 26 whether the biopsy has been performed correctly, i.e. with removal of tissue, whether this tissue has been removed in a suitable quantity, and whether it has remained in the cannula during the extraction of the needle from the patient.

Finally, having withdrawn the tissue, this is extracted from the cannula 3 in any known manner. For example, the mandrel 5 can be removed from the handgrip 2 (by passing it through the aperture 28 in the chamber 26) and a usual expulsion device be inserted into the handgrip and cannula for ejecting the tissue withdrawn by the cannula.

In FIGS. 1 and 2, the effectiveness of the biopsy and the quantity of tissue withdrawn are indicated by viewing the position of the mandrel cap 8 within the handgrip 2.

However if this viewing is difficult because of the manner in which a particular biopsy is performed, the variation in the position of the mandrel relative to the cannula can be determined electrically.

For example, as shown in FIG. 3 in which parts already described are indicated by the same reference numerals, the cap 8 acts on a variable resistor 50 to vary the voltage $V_R$ measured across its ends. The various positions of the mandrel 5 within the chamber 26 of the handgrip 2 (and hence within the cannula 3) therefore correspond to electrical signals which can be displayed on a screen which can even be some distance from the region in which the biopsy is performed.

In a further embodiment of the invention a magnetic element 51 can be associated with the cap 8 and be detected by suitable presence sensors 52 associated with the handgrip 2 and placed in various positions along its chamber 26. Again in this case, different positions of the cap 8 within this latter represent different positions of the mandrel 5 within the cannula 3 and hence different quantities of tissue removed from the patient.

Other embodiments of the invention are possible, all of which are to be considered as falling within the scope of the present invention.

I claim:

1. A device for performing a biopsy comprising: a needle having a handgrip and a cannula connected to the handgrip;
   a cannula bore within the cannula;
   a mandrel movable within the cannula bore, the mandrel having a capped end;
   a chamber located within the handgrip and being in communication with the cannula bore, the chamber having an hermetically sealed end and a communicating end, the communicating end permitting communication between the chamber and the cannula bore; and
   interception means for use with the handgrip, the interception means being capable of locking the mandrel within the cannula bore during insertion of the needle into a patient, and permitting movement of the mandrel within the cannula bore during the biopsy, whereby biopsy tissue entering the cannula bore acts on the capped end of the mandrel urging it towards and into the chamber, the extent of movement of the capped end within the chamber being measurable to indicate the quantity of tissue in the cannula bore.

2. A device as claimed in claim 1 wherein the sealed end of the chamber is provided by an edge of the handgrip.

3. A device as claimed in claim 1 wherein the cannula and handgrip are rigidly fixed to each other.

4. A device as claimed in claim 1 wherein the handgrip further comprises a channel between the chamber and the cannula bore, the channel receiving the interception means in at least two working positions, a first working position of the interception means preventing movement of the mandrel within the cannula bore, and a second working position permitting movement of the mandrel within the cannula bore.

5. A device as claimed in claim 4 wherein the channel comprises a hole having an axis substantially perpendicular to that of the cannula bore and the chamber.

6. A device as claimed in claim 4 wherein the channel defines a seat for the interception means.

7. A device as claimed in claim 4 wherein the interception means comprises a stem, a hole in the stem which registers with the cannula bore and the chamber when the interception means is in the second working position, the stem having an enlarged head at one end thereof acting as a stop for movement of the interception means within the channel and a pair of opposing arms at another end thereof, the arms being elastically deformable.

8. A device as claimed in claim 1 wherein the chamber comprises at least one transparent wall so that the interior of the chamber can be viewed.

9. A device as claimed in claim 8 wherein the transparent wall comprises spaced markings so that the position of the mandrel in the chamber and cannula bore can be determined by observing the position of the capped end of the mandrel within the chamber.

10. A device as claimed in claim 1 further comprising sensor means for determining the position of the mandrel in the cannula bore, the sensor means sensing the position of the capped end of the mandrel within the chamber.

11. A device as claimed in claim 10 wherein the sensor means comprises a variable resistor upon which the free end of the mandrel acts to vary the voltage ($V_R$) across ends of the resistor.

12. A device as claimed in claim 10 wherein the sensor means comprises at least one magnetic member associated with the free end of the mandrel, the magnetic members cooperating with presence sensors located in different positions within the chamber.

* * * * *